United States Patent [19]
Fujiyama et al.

[11] 3,948,998
[45] Apr. 6, 1976

[54] PROCESS FOR PRODUCING p-TOLUALDEHYDE

[75] Inventors: Susumu Fujiyama; Takehiko Takahashi; Shigeki Kozao, all of Niigata; Toyomi Kasahara, Kurashiki, all of Japan

[73] Assignee: Mitsubishi Gas Chemical Company, Inc., Tokyo, Japan

[22] Filed: Dec. 5, 1974

[21] Appl. No.: 530,006

[30] Foreign Application Priority Data
Dec. 21, 1973 Japan............................. 48-143101

[52] U.S. Cl. ................................................ 260/599
[51] Int. Cl.² ......................................... C07C 45/14
[58] Field of Search ...................................... 260/599

[56] References Cited
FOREIGN PATENTS OR APPLICATIONS
39-29760    1964    Japan................................ 260/599

Primary Examiner—Bernard Helfin
Attorney, Agent, or Firm—Flynn & Frishauf

[57] ABSTRACT

This invention relates to a two step process for producing p-tolualdehyde which comprises reacting toluene with carbon monoxide in the presence of hydrogen fluoride and boron trifluoride, characterized by mixing all of the toluene, all of the hydrogen fluoride and only part of the boron trifluoride necessary to convert a substantial amount of toluene to p-tolualdehyde, thereby forming a toluene-hydrogen fluoride-boron trifluoride complex and reacting the toluene in the reaction system with carbon monoxide, thereby converting a portion of the toluene to p-tolualdehyde, and then adding the remainder of the boron trifluoride to the reaction product and reacting the remainder of the toluene with carbon oxide.

9 Claims, 1 Drawing Figure

PROCESS FOR PRODUCING P-TOLUALDEHYDE

BACKGROUND OF THE INVENTION

The present invention relates to a process for producing p-tolualdehyde which comprises reacting toluene with carbon monoxide in the presence of a hydrogen fluoride-boron trifluoride catalyst.

Japanese Pat. Publication No. 29760/1964 discloses a process for producing p-tolualdehyde which comprises reacting toluene with carbon monoxide in the presence of a hydrogen fluoride-boron trifluoride catalyst. In other words, the invention of Japanese Pat. Publication No. 29760/1964 relates to a process for producing p-tolualdehyde which comprises adding all the necessary boron trifluoride to a mixture of the toluene and an excess amount of hydrogen fluoride to form a toluene-hydrogen fluoride-boron trifluoride complex and then introducing carbon monoxide to the complex to convert the toluene to p-tolualdehyde. In such process disclosed in the Japanese Patent Publication, the reaction of the carbon monoxide with the toluene is effected at a temperature below room temperature in order to avoid any change in quality of the object product, namely p-tolualdehyde. P-tolualdehyde can be produced in a good yield by adjusting the molar ratio of the catalysts to toluene to be within a determined range.

However, according to the invention of the Japanese Patent Publication, all the amount of boron trifluoride necessary to convert a substantial amount of toluene to p-tolualdehyde is introduced to a toluene-hydrogen fluoride mixture, thereby forming a toluene-hydrogen fluoride-boron trifluoride complex, and thereafter carbon monoxide is introduced to the complex to effect the reaction of toluene with carbon monoxide. In such process, since the vapor pressure of the toluene-hydrogen fluoride-boron trifluoride complex is high, it is necessary to introduce the boron trifluoride to the mixture of toluene and hydrogen fluoride at a relatively high pressure in order to add all the necessary amount of boron trifluoride to the mixture. But, since boron trifluoride which is a catalyst is highly corrosive, it is difficult to make an apparatus for compressing corrosive boron trifluoride.

It is preferable to introduce boron trifluoride to a toluene-hydrogen fluoride mixture at a pressure lower than one at which p-tolualdehyde-hydrogen fluoride-boron trifluoride complex is decomposed in a decomposition column. When all the necessary amount of boron trifluoride is added to the toluene-hydrogen fluoride mixture, the vapor pressure of the toluene-hydrogen fluoride-boron trifluoride complex becomes high. In order to introduce boron trifluoride withdrawn from the decomposition column to the toluene-hydrogen fluoride mixture without compressing it, it is necessary to raise the decomposition pressure. However when the decomposition pressure is too high, a change in quality of p-tolualdehyde and polymerization of the aldehyde are generally prone to occur in the decomposition column.

This invention eliminates the above mentioned disadvantages.

The conversion of toluene to p-tolualdehyde depends upon the amount of boron trifluoride added to the reaction system. When all the boron trifluoride necessary to convert a substantial amount of toluene to p-tolualdehyde is introduced to a toluene-hydrogen fluoride mixture, the vapor pressure of the resulting toluene-hydrogen fluoride-boron trifluoride complex becomes high.

It was found that the vapor pressure of a mixture of toluene, hydrogen fluoride and boron trifluoride is in proportion to the amount of boron trifluoride present in the mixture, especially the ratio of the boron trifluoride to the hydrogen fluoride. We, the inventors, have found that when only part of the boron trifluoride necessary to convert a substantial amount of toluene to p-tolualdehyde is introduced to a mixture of toluene and hydrogen fluoride, the vapor pressure of the mixture does not become high. Furthermore, we have found a process for introducing the necessary amount of boron trifluoride to the mixture of toluene and hydrogen fluoride at a relatively low pressure, in which part of the necessary amount of boron trifluoride is added to the mixture, and then part of the toluene reacts with the carbon monoxide, and thereafter the remainder of the boron trifluoride is added to the mixture. This invention was formed on the basis of these discoveries.

Therefore, it is an object of this invention to provide a process for producing p-tolualdehyde in which boron trifluoride to be used as a catalyst can be added to a mixture of toluene and hydrogen fluoride at a relatively low pressure.

It is a further object of the invention to provide a process for producing p-tolualdehyde in which boron trifluoride to be used as a catalyst can be introduced to the mixture at a pressure lower than one at which the decomposition of p-tolualdehyde is effected.

It is another object of the invention to provide a two-step process for producing p-tolualdehyde.

Other object of the invention will in part be obvious and will in part appear hereinafter.

SUMMARY OF THE INVENTION

This invention is explained in detail on the basis of the embodiment.

This invention provides a process for producing p-tolualdehyde in which the reaction of toluene with carbon monoxide is effected in two reactors. The present invention comprises mixing all of toluene, all of hydrogen fluoride and only part of the amount of boron trifluoride necessary to convert a substantial amount of toluene to p-tolualdehyde, thereby forming a toluene-hydrogen fluoride-boron trifluoride complex, and blowing carbon monoxide into the reaction system, thereby reacting toluene in the reaction system with carbon monoxide, thereby converting a portion of the toluene in the system to p-tolualdehyde, and then adding the remainder of the boron trifluoride to the reaction system and reacting with the remainder of the toluene with carbon monoxide, thereby converting a substantial amount of the toluene to p-tolualdehyde.

DETAILED DESCRIPTION OF THE INVENTION

Figure 1:
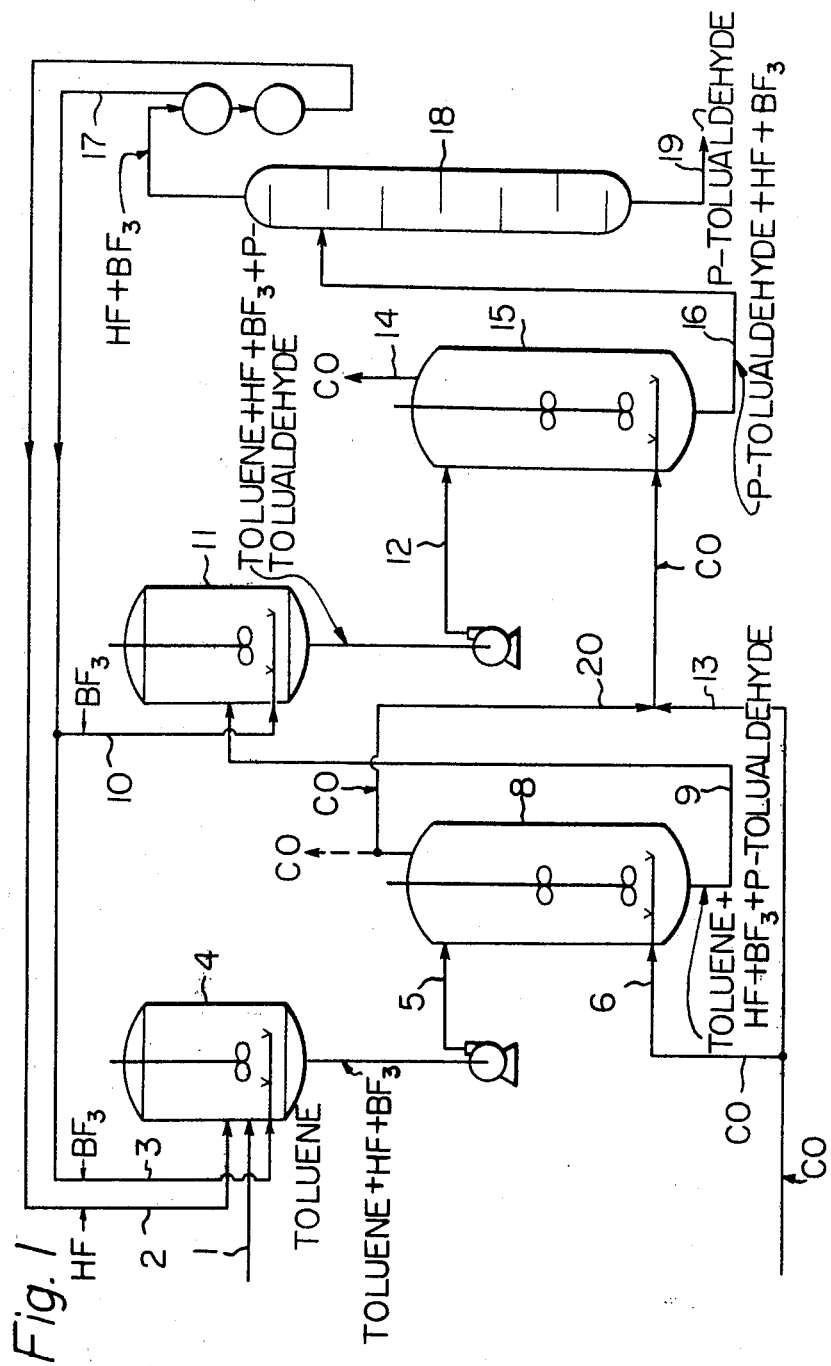

According to the present invention, not all the boron trifluoride necessary to convert a substantial amount of toluene to p-tolualdehyde is introduced to a toluene-hydrogen fluoride mixture; only part of the necessary amount of boron trifluoride is introduced to the toluene-hydrogen fluoride mixture in the blending tank connected to first reactor, whereby the vapor pressure of the resulting toluene-hydrogen fluoride-boron trifluoride complex can be kept low in the blending tank. Therefore, part of the boron trifluoride can be blown into a mixture of toluene and hydrogen fluoride at a pressure lower than one at which p-tolualdehyde-hydrogen fluoride-boron trifluoride complex is decomposed in a decomposition column. In other words, boron trifluoride can be blown into the mixture without further compressing boron trifluoride withdrawn from the decomposition column. Thereafter, the mixture of toluene, hydrogen fluoride and boron trifluoride is introduced to the first reactor. Carbon monoxide is blown into the mixture in the first reactor to react the toluene with the carbon monoxide, thereby converting a portion of the toluene to p-tolualdehyde. (Since the amount of boron trifluoride present in said complex is too small to convert a substantial amount of the toluene to p-tolualdehyde, only part of the toluene is converted to p-tolualdehyde.) Then, the reaction product containing unreacted toluene is fed into an intermediate blending tank. The remainder of the boron trifluoride is introduced to the reaction system in the intermediate blending tank.

In this case, since the bond between p-tolualdehyde and the catalyst (HF and $BF_3$) is firmer than that between toluene and the catalysts, the vapor pressure in the p-tolualdehyde-hydrogen fluoride-boron trifluoride complex is very low, and particularly the vapor pressure based on boron trifluoride in the p-tolualdehyde complex is approximately zero at a temperature below room temperature. Therefore, the vapor pressure of the reaction system in the second reactor does not become high. For this reason, the remainder of the boron trifluoride can be blown into the reaction system in the intermediate blending tank at a pressure lower than one at which p-tolualdehyde-boron trifluoride complex is decomposed in a decomposition column. The resulting solution is fed into a second reactor. Carbon monoxide is blown into the solution in the second reactor to react the remainder of the toluene with carbon monoxide.

Consequently, according to the present invention, while boron trifluoride is introduced to the mixture of toluene and hydrogen fluoride, the vapor pressure of the blending tanks can always be kept low. Furthermore, according to the present invention, p-tolualdehyde can be prepared from toluene at a relatively low pressure without reducing the rate of reaction and the yield of the product.

The formation reaction of p-tolualdehyde is based on the reaction of toluene complex with carbon monoxide. The controling factor of the reaction, namely the step determining the rate of the reaction is the diffusion rate of carbon monoxide into the complex solution. The rate of the reaction does not seem to depend directly upon the amount of catalyst, namely boron trifluoride used. However, the vapor pressure of the toluene-hydrogen fluoride-boron trifluoride complex depends upon the amount of boron trifluoride present in the complex solution. Therefore, as the vapor pressure of the complex increases, the partial pressure of carbon monoxide is lowered, thereby preventing the diffusion of carbon monoxide into the complex. Consequently the increase in the vapor pressure of the complex lowers the rate of the reaction. To the contrary, the decrease in the vapor pressure raises the rate.

The ratio of division of boron trifluoride into the blending tank connected to the first reactor and the blending tank connected to the second reactor should be determined so that the vapor pressures of the complex in the first and second blending tanks approximately becomes equal to each other. Generally, from about 40 to about 70% by weight, preferably from about 50 to about 70% by weight of boron trifluoride to be added to the total reaction system is circulated to the blending tank connected to the first reactor. The remainder of the boron trifluoride is circulated to the blending tank connected to the second reactor.

Since boron trifluoride to be added to the total reaction system is added to two blending tanks by dividing it into two portions, the vapor pressure of the toluene complex or the reacting solution in the first and second reactors can be lowered. This is preferable from the view point of having the reaction proceed smoothly.

The conversion of toluene to p-tolualdehyde depends in a great measure upon the amount of the catalysts used. That is, the larger the amount of the catalysts used is, the higher the conversion of toluene to p-tolualdehyde is. The vapor pressure of the toluene complex can be lowered by increasing the amount of hydrogen fluoride used; and the use of a large amount of hydrogen fluoride accelerates the reaction of toluene with carbon monoxide; and the use of a large amount of hydrogen fluoride is preferred from the viewpoint of circulating the catalysts. However, in case of using a large amount of hydrogen fluoride, the quantity of heat for recovering catalyst in the subsequent decomposing step, the energy required for cooling the system therefor, and the cost of apparatus for recovering the catalyst are expected to increase. Therefore, from an economic point of view, it is preferable that the amount of hydrogen fluoride used be reduced to as low an amount as possible. Consequently, the amount of hydrogen fluoride used cannot be specifically set down. When the reaction of toluene with carbon monoxide is effected under ordinary operating conditions, preferably from about 3 to about 7 mol of hydrogen fluoride and from about 1 to about 2 mol of boron trifluoride are used per 1 mol of toluene and more preferably from about 5 to about 6 mol of hydrogen fluoride and from about 1 to about 1.5 mol of boron trifluoride are used per 1 mol of toluene.

The temperature of the reaction system in each one of the two blending tanks and the first and second reactors is preferably maintained at not more than room temperature, more preferably less than 0°C in order to avoid a change in quality of the p-tolualdehyde. However, when the reaction is quickly effected, a change in quality of the p-tolualdehyde is negligible even in case of effecting the reaction at more than room temperature. Therefore, the reaction temperature is not critical. It is preferred to maintain the pressure in the blending tanks and the reaction pressure to as a low pressure as possible. If a temperature and a definite proportion of each component contained in the complex are given selected from the above mentioned ranges, the reaction pressure is automatically determined. The pressure in each of the blending tanks can easily be lowered to less than 2 atmospheric absolute ata by adjusting the proportion of the components in the complex and a proper temperature in each of the blending tanks. A reaction pressure of 7–15 ata is preferred. However, the pressures in the blending tanks or the reaction pressures cannot be specifically set down, since these pressures depend on the proportion of each component contained in the complex and the temperature in the blending tanks or the reaction temperatures.

The embodiment of the present invention is illustrated by the drawing, but this embodiment should not be deemed as limiting the practice of the present invention.

FIG. 1 is a flow sheet showing the embodiment of this invention.

FIG. 1 shows a process for producing p-tolualdehyde from toluene. Toluene as a raw material and hydrogen fluoride and boron trifluoride circulated from a decomposition step are introduced to blending tank 4 through lines 1, 2 and 3, respectively. For example, in case of adding to the total reaction system toluene, hydrogen fluoride and boron trifluoride in which the ratio of toluene:HF:BF$_3$ is 1:5:1, a toluene-hydrogen fluoride-boron trifluoride complex in which the ratio of toluene:HF:BF$_3$ is 1:5:0.5 was prepared in tank 4. The ratio of boron trifluoride to toluene is half of boron trifluoride to toluene necessary to convert a substantial amount of the toluene to p-tolualdehyde. For example, when the operating temperature in the blending tank 4 is −20°C, the operating pressure is 2 ata which is higher than the vapor pressure of the toluene complex (the ratio of toluene:HF:BF$_3$ is 1:5:0.5).

An apparatus, such as agitating tank equipped with mixer and cooler should be used as blending tank 4 so that effective mixing of liquid toluene with liquid hydrogen fluoride and effective contact of these components with gaseous boron trifluoride can be carried out and so that heat generated by the formation of complex can quickly be removed.

The toluene-hydrogen fluoride-boron trifluoride complex solution so prepared is fed into first reactor 8 through line 5, and in first reactor 8, the complex is contacted with pressurized carbon monoxide fed thereinto through line 6. The reaction of toluene with carbon monoxide in first reactor 8 is effected, for example at a temperature of 0°C and at a pressure of 10 ata. When gas-liquid contact is effected with sufficient agitation, the reaction quickly proceeds. Since the amount of boron trifluoride contained in the complex is less than the amount of boron trifluoride necessary to convert a substantial amount of toluene to p-tolualdehyde, all the toluene is not converted to a toluene-hydrogen fluoride-boron trifluoride complex. Therefore, conversion of toluene to p-tolualdehyde is low. That is, the mol of toluene more than that of boron trifluoride is not converted to p-tolualdehyde. In the complex having the ratio of each components as mentioned above, about 45% of toluene is converted to p-tolualdehyde.

However, the rate of formation of p-tolualdehyde greatly increases, because the amount of boron trifluoride present in the complex having the ratio of each components as mentioned above (the ratio of toluene:HF:BF$_3$ is 1:5:0.5) is less than the amount of boron trifluoride necessary to convert a substantial amount of toluene to p-tolualdehyde. The reason is as follows:

The rate of the formation of p-tolualdehyde or the absorption of carbon monoxide depends upon the diffusion rate of carbon monoxide, that is the rate of the reaction depends upon the partial pressure of carbon monoxide in the first reactor 8. When the amount of boron trifluoride present in the complex is small, the vapor pressure of the complex which is in proportion to the amount of boron trifluoride present in the complex is small, whereby the partial pressure of carbon monoxide becomes large. Therefore, though the amount of boron trifluoride present in the complex having the ratio of each component as mentioned above (the ratio of toluene:HF:BF$_3$ is 1:5:0.5) is less than the amount of boron trifluoride necessary to convert a substantial amount of the toluene to p-tolualdehyde, the rate of the reaction of toluene with carbon monoxide increases.

On the other hands, when the amount of boron trifluoride necessary to convert a substantial amount of toluene to p-tolualdehyde is present in the complex, the vapor pressure of the complex is high. Therefore, the partial pressure of carbon monoxide is low, and consequently the rate of the reaction is small. When using the complex in which the content of boron trifluoride is high, the reaction cannot be effected at the same rate of reaction as in the case of using the complex in which the content of boron trifluoride is low, unless the reaction pressure is raised.

In carrying out the reaction, agitation of the reaction solution is necessary to promote the diffusion of carbon monoxide and to cool the reaction solution for preventing a raise in the temperature caused by the reaction heat generated. In particular, a raise in the reaction temperature should be avoided to prevent a change in the quality of the product. Therefore, a reactor, such as an agitation tank equipped with external cooler, a multi-plate agitation tank, foaming column, or a reactor of pipe type can be used.

The reaction solution obtained by the reaction in the first reactor contains p-tolualdehyde as a reaction product and a considerable amount of the unreacted toluene.

The resulting reaction solution is withdrawn from first reactor 8 and is fed into intermediate blending tank 11 through line 9, and in tank 11 the reaction solution is contacted with the remainder of the necessary amount of boron trifluoride, whereby the unreacted toluene in the reaction solution ca easily be formed to a toluene-hydrogen fluoride-boron trifluoride complex. In other words, the operating step in intermediate tank 11 is similar to the operating step in tank 4, and up to 1 mol of boron trifluoride is fed into the toluene complex per 1 mol of toluene employed as a raw material at a temperature of −20°C at a pressure of from 2 to 2.5 ata.

The resulting complex is fed into second reactor 15 through line 12. Carbon monoxide is fed into reactor 15, and the reaction of the carbon monoxide with the toluene in the complex is smoothly effected at a temperature of 0°C at a pressure of 10 ata. Carbon monoxide from a carbon monoxide source (not shown) may be introduced to reactor 15 through line 13, or the unreacted carbon monoxide from first reactor 8 may be introduced to second reactor 15, or the mixed carbon monoxide from both sources may be used. When carbon monoxide contains inert impurities, the inert impurities are purged through line 14 after the concentration of the inert impurities reaches the condensed concentration. Finally, after the reaction in second reactor 15 completed, highly efficient conversion of toluene to p-tolualdehyde can be attained. The reaction product, that is, the p-tolualdehyde-hydrogen fluoride-boron trifluoride complex, is withdrawn through line 16 and is fed into decomposition column 18. In column 18, the complex is subjected to thermal decomposition to obtain p-tolualdehyde, hydrogen fluoride and boron trifluoride, separately.

Hydrogen fluoride decomposed and separated in column 18 is circulated to blending tank 4 through line 2. Boron trifluoride decomposed and separated in column 18 is divided into two parts, and one is fed to tank 4, and the other is fed to tank 11. P-tolualdehyde which is the end product is withdrawn from the bottom of column 18 through line 19.

It is preferable that the structure of the decomposition column be such that the catalyst components may be completely withdrawn as soon as possible. The decomposition of p-tolualdehyde complex in the decomposition column is effected at such an elevated temperature that the p-tolualdehyde complex can be decomposed, for example at a temperature of at least 110°C. Also, decomposition is effected at a pressure above the operating pressure in tanks 4 and 11, for example, at a pressure of 3 ata. When the pressure in the decomposition column is higher than the operating pressure in blending tanks 4 and 11, the use of compressor for circulating boron trifluoride generated from the decomposition column becomes unnecessary. This is a great economic advantage when the present invention is used on a commercial basis.

As mentioned above, this invention is characterized by adding one portion of boron trifluoride to blending tank 4 for feeding reactants to the first reactor and adding the other of boron trifluoride to intermediate blending tank 11 positioned between the first and second reactors, whereby the operating pressure of blending tanks 4 and 11 can be lowered. Therefore, the pressure necessary for circulating boron trifluoride to blending tanks 4 and 11, that is the pressure in the decomposition column, can be lowered, and the pressure necessary for feeding carbon monoxide to the reactor can also be lowered. When the pressure in the decomposition column is considerably higher than the vapor pressure of the complex in the reactor, energy for cooling tank 4 can be saved by raising the operating temperature in tank 4 in place of lowering the pressure in the decomposition column.

This invention is further illustrated, but in no way limited, by the following Examples.

EXAMPLES 1 AND 2 AND COMPARATIVE EXAMPLES 1 AND 2

According to the process as illustrated in FIG. 1, p-tolualdehyde was produced. The operating conditions and the amount of each reactant, catalyst and product fed or withdrawn are given in Table 1.

The results obtained by adding all the necessary amount of boron trifluoride to hydrogen fluoride and toluene without dividing boron trifluoride into two parts are given in Table 1 as Comparative Examples 1 and 2.

Table 1

| | | Tank 4 | First reactor | Intermediate tank 11 | Second reactor | Decomposition column |
|---|---|---|---|---|---|---|
| Example 1 | Amount of toluene supplied (mol) | 1.0 | 1.0 | 0.55 | 0.55 | 0.25 |
| | Amount of HF supplied (mol) | 4.7 | 4.7 | 5.0 | 5.0 | 5.0 |
| | Amount of $BF_3$ supplied (mol) | 0.5 | 0.5 | 1.0 | 1.0 | 1.0 |
| | Amount of p-tolualdehyde produced (mol) | 0 | 0 | 0.45 | 0.45 | 0.25 |
| | Temperature (°C) | −20 | 0 | −20 | 0 | 140 |
| | Pressure (ata) | 2.0 | 10 | 2.5 | 10 | 3 |
| Comparative Example 1 | Amount of toluene supplied (mol) | 1.0 | 1.0 | — | — | 0.25 |
| | Amount of HF supplied (mol) | 5.0 | 5.0 | — | — | 5.0 |
| | Amount of $BF_3$ supplied (mol) | 1.0 | 1.0 | — | — | 1.0 |
| | Amount of p-tolualdehyde produced (mol) | 0 | 0 | — | — | 0.75 |
| | Temperature (°C) | −20 | 0 | — | — | 140 |
| | Pressure (ata) | 4.0 | 15 | — | — | 5 |
| Example 2 | Amount of toluene supplied (mol) | 1.0 | 1.0 | 0.40 | 0.40 | 0.10 |
| | Amount of HF supplied (mol) | 4.5 | 4.5 | 5.0 | 5.0 | 5.0 |
| | Amount of $BF_3$ supplied (mol) | 0.7 | 0.7 | 1.3 | 1.3 | 1.3 |
| | Amount of p-tolualdehyde produced (mol) | 0 | 0 | 0.6 | 0.6 | 0.90 |
| | Temperature (°C) | −30 | 0 | −30 | 0 | 140 |
| | Pressure (ata) | 2.0 | 15 | 2.0 | 15 | 3 |
| | Amount of toluene supplied (mol) | 1.0 | 1.0 | — | — | 0.10 |
| | Amount of | | | | | |

Table 1-continued

|  |  | Tank 4 | First reactor | Intermediate tank 11 | Second reactor | Decomposition column |
|---|---|---|---|---|---|---|
| Comparative Example 2 | HF supplied (mol) | 5.0 | 5.0 | — | — | 5.0 |
|  | Amount of $BF_3$ supplied (mol) | 1.3 | 1.3 | — | — | 1.3 |
|  | Amount of p-tolualdehyde produced (mol) | 0 | 0 | — | — | 0.9 |
|  | Temperature (°C) | −30 | 0 | — | — | 140 |
|  | Pressure (ata) | 4.0 | 20 | — | — | 5 |

What we claim is:

1. A process for producing p-tolualdehyde which comprises reacting toluene with carbon monoxide in the presence of hydrogen fluoride and boron trifluoride, characterized by (1) mixing all of the toluene, all of the hydrogen fluoride and part of the boron trifluoride, thereby forming a toluene-hydrogen fluoride-boron trifluoride complex solution, and adding carbon monoxide to the solution to react the toluene with carbon monoxide, thereby converting a portion of the toluene to p-tolualdehyde, and then (2) adding the remainder of the boron trifluoride to the reaction system and reacting the remainder of the toluene with carbon monoxide, thereby converting a substanial amount of the toluene to p-tolualdehyde, the amounts of boron trifluoride in (1) and (2) being divided such that the vapor pressures of the complex in (1) and (2) are substantially equal.

2. A process for producing p-tolualdehyde which comprises reacting toluene with carbon monoxide in the presence of hydrogen fluoride and boron trifluoride, characterized by (1) mixing toluene, hydrogen fluoride and only part of the boron trifluoride necessary to convert a substantial amount of the toluene to p-tolualdehyde, thereby forming a toluene-hydrogen fluoride-boron trifluoride complex, and reacting the toluene in the solution with carbon monoxide, thereby converting a portion of the toluene in the complex to p-tolualdehyde, and (2) then adding the remainder of the boron trifluoride to the reaction system and reacting the remainder of the toluene in the complex with carbon monoxide, thereby converting a substantial amount of the toluene to p-tolualdehyde, the amounts of boron trifluoride in (1) and (2) being divided such that the vapor pressures of the complex in (1) and (2) are substantially equal.

3. The process defined in claim 2, wherein from about 1 to about 2 mols of boron trifluoride are used per 1 mol of toluene.

4. The process defined in claim 2, wherein from about 1 to about 1.5 mols of boron trifluoride are used per 1 mol of toluene.

5. The process defined in claim 2, wherein from about 40 to about 70% by weight of boron trifluoride to be used is first added to a toluene-hydrogen fluoride mixture, and after a portion of the toluene is converted to p-tolualdehyde, the remainder of the boron trifluoride is added to the reaction system.

6. The process defined in claim 2, wherein from about 3 to about 7 mols of hydrogen fluoride are used per mol of toluene.

7. The process defined in claim 2, wherein from about 5 to about 6 mols of hydrogen fluoride are used per mol of toluene.

8. The process defined in claim 2, wherein the temperature in (1) is less than about 0°C.

9. The process defined in claim 2, wherein the temperature in (2) is less than about 0°C.

* * * * *